(12) United States Patent
Yamaguchi et al.

(10) Patent No.: US 10,195,301 B2
(45) Date of Patent: *Feb. 5, 2019

(54) INK COMPOSITION FOR DETECTING HYDROGEN PEROXIDE AND INDICATOR FOR DETECTION OF HYDROGEN PEROXIDE

(71) Applicant: SAKURA COLOR PRODUCTS CORPORATION, Osaka-shi, Osaka (JP)

(72) Inventors: Norihiro Yamaguchi, Sakai (JP); Kyoko Ohwaki, Nara (JP)

(73) Assignee: SAKURA COLOR PRODUCTS CORPORATION, Osaka-shi (JP)

( * ) Notice: Subject to any disclaimer, the term of this patent is extended or adjusted under 35 U.S.C. 154(b) by 276 days.

This patent is subject to a terminal disclaimer.

(21) Appl. No.: 14/922,489

(22) Filed: Oct. 26, 2015

(65) Prior Publication Data

US 2016/0045631 A1 Feb. 18, 2016

Related U.S. Application Data

(63) Continuation of application No. 11/989,852, filed as application No. PCT/JP2006/315214 on Aug. 1, 2006, now Pat. No. 9,194,808.

(30) Foreign Application Priority Data

Aug. 2, 2005 (JP) .................................. 2005-224098

(51) Int. Cl.
| | |
|---|---|
| *G01N 21/75* | (2006.01) |
| *A61L 2/28* | (2006.01) |
| *A61L 2/14* | (2006.01) |
| *G01N 21/78* | (2006.01) |
| *G01N 31/22* | (2006.01) |
| *C08K 5/3417* | (2006.01) |
| *C09D 11/00* | (2014.01) |
| *C09D 125/08* | (2006.01) |

(52) U.S. Cl.
CPC ........ *A61L 2/28* (2013.01); *A61L 2/14* (2013.01); *C08K 5/3417* (2013.01); *C09D 11/00* (2013.01); *C09D 125/08* (2013.01); *G01N 21/783* (2013.01); *G01N 31/22* (2013.01)

(58) Field of Classification Search
None
See application file for complete search history.

(56) References Cited

U.S. PATENT DOCUMENTS

| | | |
|---|---|---|
| 4,605,441 A | 8/1986 | Masuda et al. |
| 5,116,409 A | 5/1992 | Moffatt |
| 5,482,684 A | 1/1996 | Martens et al. |
| 6,267,242 B1 | 7/2001 | Nagata et al. |
| 6,336,964 B1 | 1/2002 | Omatsu et al. |
| 6,659,036 B2 | 12/2003 | Omatsu et al. |
| 7,189,355 B2 | 3/2007 | Mikumo et al. |
| 7,981,687 B2 | 7/2011 | Yamaguchi et al. |
| 2001/0054374 A1 | 12/2001 | Omatsu et al. |
| 2002/0121629 A1 | 9/2002 | Mikumo et al. |
| 2003/0194346 A1 | 10/2003 | Read |
| 2006/0160009 A1 | 7/2006 | Padunchwit et al. |

FOREIGN PATENT DOCUMENTS

EP 1023598 B1 7/2005

OTHER PUBLICATIONS

European Search Report dated Feb. 15, 2011, issued in corresponding European Patent Application No. 06782092.8.
International Search Report of PCT/JP2006/315214 dated Sep. 5, 2006.

*Primary Examiner* — Dennis White
(74) *Attorney, Agent, or Firm* — Westerman, Hattori, Daniels & Adrian, LLP

(57) ABSTRACT

A primary object of the present invention is to provide a hydrogen peroxide gas detection indicator which allows more certain visual recognition of color changing according to the concentration of hydrogen peroxide gas. The structure of this invention relates to an ink composition for detecting hydrogen peroxide gas containing (1) at least one of styrene acrylic resins and styrene-maleic acid resins and (2) a methine dye. According to this invention, a color-changing layer is formed using the ink composition for detecting hydrogen peroxide gas, allowing color changing according to the concentration of hydrogen peroxide gas to be visually recognized.

17 Claims, No Drawings

INK COMPOSITION FOR DETECTING HYDROGEN PEROXIDE AND INDICATOR FOR DETECTION OF HYDROGEN PEROXIDE

CROSS-REFERENCE TO RELATED APPLICATIONS

This application is a Continuation of U.S. application Ser. No. 11/989,852, filed Jan. 31, 2008, and wherein application Ser. No. 11/989,852 is a national stage application filed under 35 USC § 371 of International Application No. PCT/JP2006/315214, filed Aug. 1, 2006, and which is based upon and claims the benefit of priority from the prior Japanese Patent Application No. JP 2005-224098, filed on Aug. 2, 2005, the entire contents of which are incorporated herein by reference.

TECHNICAL FIELD

The present invention relates to an ink composition for detecting hydrogen peroxide gas and an indicator for hydrogen peroxide gas detection.

BACKGROUND ART

Various kinds of instruments, appliances, etc., used at hospitals, laboratories, etc., are sterilized for disinfection. Typical sterilization treatment procedures include a sterilization treatment using hydrogen peroxide gas.

In this sterilization treatment, an indicator needs to be installed to confirm whether the sterilization treatment is complete. In more detail, it is necessary to install, in a sterilizer, an indicator whose color changes in response to the atmospheric gas concentration in a processing system and to the exposure time.

As a prior-art technique for such an indicator, known is, for example, a method in which the progress of sterilization is detected when an indicator using bromophenol blue, which is a pH indicator, turns from light blue to dark blue due to the action of peracetic acid or acetic acid gas when monitoring a sterilizing process in, for example, low-temperature gas plasma sterilization using gas comprising peracetic acid and acetic acid as principal components, (Patent-Document 1).

Further, an indicator for use in plasma sterilization which comprises a coloring matter, a color changing auxiliary, and a binder and which exhibits change in the color tone due to plasma sterilization is known (Patent Documents 2 and 3)

Furthermore, an ink composition for detecting plasma sterilization comprising an anthraquinone-based dye having at least one amino group selected from a primary amino group and a secondary amino group is known (Patent Document 4).

[Patent Document 1] U.S. Pat. No. 5,482,684.
[Patent Document 2] Japanese Unexamined Patent Publication No. 1999-178904.
[Patent Document 3] Japanese Unexamined Patent Publication No. 2002-11081.
[Patent Document 4] Japanese Unexamined Patent Publication No. 2001-174449.

Disclosure of the Invention Problem to be Solved by the Invention

When the indicator of the above-mentioned Patent Document 1 is left in the sterilization device after the color has changed due to sterilization, the changed color sometimes returns to the initial color. Thus, the indicator of the above-mentioned Patent Document 1 has a problem with stability after the color changed. When the changed color of the indicator returns to the initial color, it is impossible to confirm whether articles, instruments, and the like, which are placed in the device, are effectively sterilized.

The techniques disclosed in Patent Documents 2 to 4 need to be improved in terms of detection sensitivity and detection accuracy. More specifically, these indicators change the colors relatively rapidly at an early stage of their exposure to hydrogen peroxide gas; the color sometimes changes before sterilization is complete. In particular, the diffusion degree of hydrogen peroxide gas in the device fluctuates depending on the dimensions, shapes, substance, etc., of the material to be processed and there is a possibility that malfunction of the indicator occur when the hydrogen peroxide gas concentrations become different (lower or higher) at different portions of the material being sterilized.

Therefore, a main object of the present invention is to provide an indicator for hydrogen peroxide gas detection by which the change in color according to the concentration of the hydrogen peroxide gas can be visually recognized with greater accuracy.

Means for Solving the Problem

The present inventors carried out extensive research in order to solve the problems of the prior-art techniques, and found that the above-described object can be attained by employing an ink of a specific composition. Thus, the present invention has been accomplished based on the new finding.

The present invention relates to the following ink compositions for detecting hydrogen peroxide gas and indicators for hydrogen peroxide gas detection.

1. An ink composition for detecting hydrogen peroxide gas comprising 1) at least one of styrene acrylic resins and styrene-maleic acid resins, and 2) a methine dye.

2. An ink composition for detecting hydrogen peroxide gas according to item 1, further comprising a cationic surfactant.

3. An ink composition for detecting hydrogen peroxide gas according to item 2, wherein the cationic surfactant is at least one species selected from alkyltrimethylammonium salts, isoquinolinium salts, imidazolinium salts, and pyridinium salts.

4. An ink composition for detecting hydrogen peroxide gas according to any one of items 1 to 3, further comprising an extender.

5. An Ink composition for detecting hydrogen peroxide gas according to item 4, wherein a part or all of the extender is composed of silica.

6. An ink composition for detecting hydrogen peroxide gas according to any one of items 1 to 5, further comprising a resin binder excluding styrene acrylic resin and styrene-maleic acid resin.

7. An ink composition for detecting hydrogen peroxide gas according to any one of items 1 to 6, further comprising at least one of coloring matters whose colors do not change in a hydrogen peroxide gas atmosphere.

8. An indicator for hydrogen peroxide gas detection, comprising a color-changing layer including an ink composition according to any one of items 1 to 7.

9. An indicator according to item 8, further comprising a non-color-changing layer whose color does not change in a hydrogen peroxide gas atmosphere.

10. An indicator according to item 8 or 9, wherein the color-changing layer has features:

(1) difference between a color difference value $\Delta_{2mg}$ before and after the exposure to 2 mg/L of hydrogen peroxide gas for 6 minutes at a temperature of 50° C. and a color difference value &Brag before and after the exposure to 18 mg/L of hydrogen peroxide gas for 6 minutes at a temperature of 50° C. is 5 or more, and (2) difference between a color difference value $\Delta 18_{mg}$ before and after the exposure to 18 mg/L of hydrogen peroxide gas for 6 minutes at a temperature of 50° C. and a color difference value $\Delta_{36mg}$ before and after the exposure to 36 mg/L of hydrogen peroxide gas for 6 minutes at a temperature of 50° C. is 5 or more.

11. A packaging body for use in hydrogen peroxide gas sterilization, comprising an indicator according to any one of items 8 to 10 formed on an inner surface of a gas permeable packaging body.

12. A packaging body according to item 11, wherein a transparent aperture is provided in a part of the packaging body in such a manner that the indicator can be checked from the outside.

13. A packaging body according to item 11 or 12, wherein the gas permeable packaging body is formed of polyethylene fiber.

14. A hydrogen peroxide gas sterilization method comprising the steps of:

charging a material to be treated into a packaging body according to any one of items 11 to 13;

sealing the packaging body charged with the material to be treated; and placing the packaging body in a hydrogen peroxide plasma sterilization atmosphere.

15. A method according to item 14, wherein the packaging body is kept in the hydrogen peroxide gas sterilization atmosphere until the color of the color-changing layer of the indicator changes.

EFFECT OF THE INVENTION

The ink composition and the indicator using the same according to the present invention comprise a combination of 1) at least one of styrene acrylic resin and styrene-maleic acid resin and 2) methine dye. Thus, the present invention using the ink composition achieves an effect that changes in the color of a color-changing layer can be visually recognized, relative to the concentration and the like of hydrogen peroxide gas. More specifically, in prior-art techniques, it is difficult to visually recognize the gradual change in color at an early stage of hydrogen peroxide gas exposure because the speed at which it changes is too fast. In contrast, according to the color-changing layer of the present invention, the concentration of hydrogen peroxide gas and the color-changing degree can be correlated to a certain degree, and thus it becomes possible to gradually change the color in relation to the concentration of hydrogen peroxide gas.

DETAILED DESCRIPTION OF THE INVENTION

1. Ink Composition for Detecting Hydrogen Peroxide Gas

The ink composition for detecting hydrogen peroxide gas of the invention comprises 1) at least one of styrene acrylic resins and styrene-maleic acid resins and 2) a methine dye.
Methine Dye The composition of the present invention comprises at least one methine dye as a colorant (color changing coloring matter). As a methine dye, any dyes having one or more methine groups may be used. Thus, polymethine dyes, cyanine dyes, etc., are usable in the present invention as a methine dye. Such dyes can be suitably selected from known or commercially available methine dyes. The following are typical examples:

C.I. Basic Red 12, C.I. Basic Red 13, C.I. Basic Red 14, C.I. Basic Red 15, C.I. Basic Red 27, C.I. Basic Red 35, C.I. Basic Red 36, C.I. Basic Red 37, C.I. Basic Red 45, C.I. Basic Red 48, C.I. Basic Yellow 11, C.I. Basic Yellow 12, C.I. Basic Yellow 13, C.I. Basic Yellow 14, C.I. Basic Yellow 21, C.I. Basic Yellow 22, C.I. Basic Yellow 23, C.I. Basic Yellow 24, C.I. Basic Violet 7, C.I. Basic Violet 15, C.I. Basic Violet 16, C.I. Basic Violet 20, C.I. Basic Violet 21, C.I. Basic Violet 39, and C.I. Basic Blue 62, C.I. Basic Blue 63, etc. These can be used alone or in combination of two or more.

The content of the above-mentioned dye can be suitably determined according to a desired hue, etc.; it is usually about 0.05 to about 5% by weight, and preferably 0.1 to 1% by weight.

In the present invention, dyes or pigments other than methine dyes may also coexist. In particular, coloring matter components (hereinafter referred to as "non-color changing coloring matters") whose colors do not change in a hydrogen peroxide gas atmosphere may be contained. Thus, the visual recognition effect can be further improved due to the change in the color tone from a certain color to another color. As anon-color-changing coloring matter, known inks (normal color inks) can be used. The content of the non-color-changing color matter may be suitably determined according to the type, etc., of the non-color-changing color matter.
Styrene Acrylic Resin, Styrene-maleic Acid Resin The composition of the present invention contains at least one of styrene acrylic resins and styrene-maleic acid resins. The use of these resins makes it possible to effectively adjust the reaction rate (color changing rate) of a dye, give adhesiveness to a color-changing layer, etc.

There are no limitations on the types and properties of styrene acrylic resins and styrene-maleic acid resins, and known or commercially available resins can be used.

The content of styrene acrylic resin and/or styrene-maleic acid resin can be suitably determined according to the types and the like of the color matter to be used; it is usually about 50% by weight or less, and preferably 1 to 35% by weight.
Cationic Surfactant It is preferable for the ink composition of the invention to contain a cationic surfactant. The cationic surfactant is not limited, but it is preferable to use at least one of alkylammonium salts, isoquinolinium salts, imidazolinium salts, and pyridinium salts. Known or commercially available cationic surfactants can be used. According to the present invention, more excellent detection sensitivity can be attained by using these cationic surfactants in combination with the aforementioned colorant.

Among alkylammonium salts, alkyltrimethylammonium salt, dialkyldimethylammonium salt, etc., are preferable. Specific examples are coco-alkyltrimethylammonium chloride, beef tallow alkyltrimethylammonium chloride, behenyltrimethylammonium chloride, hexadecyltrimethylammonium chloride, lauryltrimethylammonium chloride, octadecyltrimethylammonium chloride, dioctyldimethylammonium chloride, distearyldimethylammonium chloride, alkylbenzyldimethylammonium chloride, etc.

In particular, coco-alkyltrimethylammonium chloride, lauryltrimethylammonium chloride, etc., are preferable.

Examples of isoquinolinium salts include laurylisoquinolinium bromide, cetylisoquinolinium bromide, cetylisoquinolinium chloride, laurylisoquinolinium chloride, etc. Among the above, lauryl isoquinolinium bromide is preferable.

Examples of imidazolinium salts include 1-hydroxyethyl 2-oleyl imidazolinium chloride, 2-chloro-1,3-dimethyl imidazolinium chloride, etc. among the above, 2-chloro-1,3-dimethyl imidazolinium chloride is particularly preferable.

Examples of pyridinium salts include, for example, pyridinium chloride, 1-ethylpyridinium bromide, hexadecylpyridinium chloride, cetylpyridinium chloride, 1-butylpyridinium chloride, N-n-butylpyridinium chloride, hexadecylpyridinium bromide, N-hexadecylpyridinium bromide, 1-dodecylpyridinium chloride, 3-methylhexylpyridinium chloride, 4-methylhexylpyridinium chloride, 3-methyloctylpyridinium chloride, 2-chloro-l-methylpyridinium iodide, 3,4-dimethylbutylpyridinium chloride, n-hexadecylpyridinium chloride-hydrate N-(cyanomethyl) pyridinium chloride, N-acetonylpyridinium bromide, 1-(aminoformylmethyl)pyridinium chloride, 2-amidopyridinium chloride, 2-aminopyridinium chloride, N-aminopyridinium iodide, 1-aminopyridinium iodide, 1-acetonylpyridinium chloride, N-acetonylpyridinium bromide, etc. Among the above, hexadecylpyridinium chloride is particularly preferable.

The content of the cationic surfactant can be suitably determined according to the types and the like of the above-mentioned surfactants and the colorant to be used. In general, the content of the cationic surfactant in the composition of the present invention is preferably about 0 to 15% by weight, more preferably about 0.1 to 10% by weight.

Resin Binder, Extender, Etc.

The ink composition of the invention may contain, as required, components used for known inks, such as a resin binder (excluding styrene acrylic resin and styrene-maleic acid resin), an extender, a solvent, a leveling agent, an antifoaming agent, a UV absorber, a surface controller, etc.

The resin binder may be suitably selected according to the types and the like of substrate, and known resin components for use in ink compositions for writing, printing, etc., can be utilized. Examples of resin binders are polyamide resin, maleic acid resin, ketone resin, alkylphenol resin, rosin modified resin, polyvinyl butyral, cellulose-based resin, polyester-based resin, styrene-maleic acid resin, styrene acrylic acid resin, acrylic resin, etc.

The content of the resin binder can be suitably determined according to the types of the resin binder, the colorant to be used, and the like. In general, the content of the resin binder in the composition of the present invention is preferably about 50% by weight or less, and more preferably 5 to 35% by weight.

The extender is not limited in kinds, and inorganic materials, such as bentonite, activated clay, aluminum oxide, silica, silica gel, etc., can be used. In addition, materials known as extender pigments can be used. Among the above, at least one of silica, silica gel, and alumina is preferable.

In particular, silica is more preferable. When silica is used, a plurality of cracks can be effectively produced, particularly on the surface of the color-changing layer. As a result, the detection sensitivity of the indicator can be further improved.

The content of the extender can be suitably determined according to the types of the extender to be used, the colorant to be used, and the like. The content of the extender in the composition of the present invention is generally about 0 to 30% by weight, and preferably 0.5 to 20% by weight.

Any solvents can be used in the invention insofar as they are those used in ink compositions for printing, writing, etc. Usable solvents are alcohol-based or polyhydric alcohol-based, ester-based, ether-based, ketone-based, hydrocarbon-based, glycol ether-based alcohols, and the like. Any one of the above may be suitably selected in consideration of the solubility of the colorant, the resin-based binder to be used, and the like.

The content of the solvent can be suitably determined according to the types of the solvent, the colorant to be used, and the like. The content of the solvent in the composition of the present invention is usually about 40 to 95% by weight, preferably 60 to 90% by weight.

These components are simultaneously or sequentially incorporated, and uniformly mixed using known stirrers, such as a homogenizer, dissolver, etc. For example, the above-mentioned colorant, and, as required, the above-mentioned cationic surfactant, resin-based binder, extender, etc., are sequentially added to a solvent, and the resultant mixture are mixed and stirred with a stirrer.

2. Indicator for Hydrogen Peroxide Gas Detection

The indicator of the present invention is provided with a color-changing layer that includes the ink composition of the invention described above. Usually, the color-changing layer is formed by applying or printing the ink composition of the invention onto a base material. Any substrates can be used insofar as the color-changing layer can be formed thereon. For example, metal S or alloys, ceramics, glass, concrete, plastics (polyethylene terephthalate $_{(PET)}$, polypropylene, nylon, polystyrene, etc.), fibers (nonwoven fabrics, textile fabrics, other fiber sheets), composite materials thereof, etc., can be used. Moreover, synthetic resin fiber papers (synthetic papers), such as polypropylene synthetic papers, polyethylene synthetic papers, etc., can also be suitably used.

In addition to substances whose colors change to other colors, substances whose colors fade or decolorize are also encompassed by the color-changing layer of the present invention.

The color-changing layer can be formed using the ink composition of the present invention according to known printing methods, such as silk screen printing, gravure printing, offset printing, relief printing, flexographic printing, etc. The color-changing layer can also be formed by various methods other than printing methods. For example, the color-changing layer can be formed by immersing a base material into an ink composition. Such methods are particularly preferable for materials into which ink permeates, such as nonwoven fabrics.

It is preferable for the color-changing layer to show the following features: (1) difference between a color difference value $\Delta_{2mg}$ before and after the exposure to 2 mg/L of hydrogen peroxide gas for 6 minutes at a temperature of 50° C. and a color difference value $\Delta_{18mg}$ before and after the exposure to 18 mg/L of hydrogen peroxide gas for 6 minutes at a temperature of 50° C. is 5 or more (preferably 8 or more), and (2) difference between a color difference value $\Delta_{18mg}$ before and after the exposure to 18 mg/L of hydrogen peroxide gas for 6 minutes at a temperature of 50° C. and a color difference value $\Delta_{36mg}$ before and after the exposure to 36 mg/L of hydrogen peroxide gas for 6 minutes at a temperature of 50° C. is 5 or more (preferably 8 or more) When such a color changing degree is maintained, the change in color can be visually recognized with greater accuracy. More specifically, a gradual color-changing ability that allows detection with the naked eye can be attained. Such color changing ability can be attained by the combination of (1) at least one of styrene acrylic resins and styrene-maleic acid resins and (2) a methine dye.

In the present invention, a non-color-changing layer whose color does not change in a hydrogen peroxide plasma sterilization atmosphere may be further formed on the substrate and/or on the color-changing layer. The non-color-changing layer can generally be formed of commercially-available normal color inks For example, water-based inks, oil-based inks, solventless inks, etc., can be used. The ink for use in the formation of the non-color-changing layer may optionally contain components used in known inks, such as resin binders, extenders, solvents, etc.

The non-color-changing layer may be formed in the same manner as in the case of the color-changing layer. For example, the non-color-changing layer can be formed using normal color inks according to known printing methods, such as silk screen printing, gravure printing, offset printing, relief printing, flexographic printing, etc. There are no limitations on the order of printing the color-changing layer and the non-color-changing layer, and this may be suitably determined according to the design to be printed and the like.

In the indicator of the present invention, the color-changing layer and the non-color-changing layer each may be single or plural. Two or more color-changing layers may be laminated with each other or two or more non-color-changing layers may be laminated with each other. The compositions of the color-changing layers may be the same or different. Similarly, the compositions of the non-color-changing layers may be the same or different.

Furthermore, the color-changing layer and the non-color-changing layer May be formed entirely or partially on the substrate or on each layer. In these cases, in order for, in particular, the color-changing layer to reliably change color, the color-changing layer and the non-color-changing layer are formed in such a manner that a part or all of at least one color-changing layer is exposed to a hydrogen peroxide gas atmosphere.

In the present invention, the color-changing layer and the non-color-changing layer may be freely combined insofar as completion of the hydrogen peroxide gas sterilization process can be confirmed. For example, the color-changing layer and the non-color-changing layer can be formed so that the color difference therebetween cannot be identified until the color of the color-changing layer changes or so that the color difference therebetween does not disappear until the color of the color-changing layer changes. It is preferable to form the color-changing layer and the non-color-changing layer so that the color difference therebetween cannot be identified until the color of the color-changing layer changes.

To enable the color difference to be recognized, the color-changing layer and the non-color-changing layer may be formed, for example, in such a manner that at least one character, pattern, or symbol does not appear until the color of the color-changing layer changes. In the present invention, characters, patterns, and symbols include all information notifying a change in color. The characters and the like may be suitably designed according to the intended use, etc.

Moreover, the colors of the non-color-changing layer and the color-changing layer before color changing may be different from each other. For example, the colors of the color-changing layer and the non-color-changing layer may be substantially the same, and the color difference (contrast) between the color-changing layer and the non-color-changing layer is not recognizable until the color changes.

According to the indicator of the present invention, the color-changing layer and the non-color-changing layer can be formed so that the color-changing layer and the non-color-changing layer may not be laminated This can reduce the amount of ink required.

In the present invention, a color-changing layer or non-color-changing layer can be further formed on at least one of the color-changing layer and the non-color-changing layer. For example, when a color-changing layer having a different design is formed on a layer (referred to as "a color changing/non-color-changing layer") on which the color-changing layer and the non-color-changing layer are formed in such a manner that the color-changing layer and the non-color-changing layer may not be laminated, the boundary between the color-changing layer and the non-color-changing layer in the color changing/non-color-changing layer cannot be substantially recognized. Thus, an excellent design appeal can be attained.

The indicator of the present invention can be applied to any sterilization treatment performed in a hydrogen peroxide gas atmosphere. Thus, the indicator is useful as an indicator in a hydrogen peroxide gas sterilization apparatus (specifically, an apparatus which sterilizes by generating plasma in an oxidizing gas atmosphere, such as hydrogen peroxide). When using the indicator of the present invention, for example, the indicator is placed in a commercially-available sterilizer, and may be exposed to a sterilization atmosphere together with products, articles, and the like to be sterilized. In this case, the change in the color of the indicator placed in the apparatus makes it possible to gradually detect that predetermined plasma sterilization is performed.

3. Packaging Body

The present invention includes a packaging body for hydrogen peroxide gas sterilization in which the indicator of the present invention is provided on the inner surface of a gas permeable packaging body.

As the gas permeable packaging body, preferable is a packaging body in which hydrogen peroxide gas sterilization can be carried out while enclosing a material to be processed therein. Known or commercially available gas permeable packaging bodies (pouches) used in the conventional plasma sterilization can be used. For example, packaging bodies formed of polyethylene fibers (polyethylene synthetic paper) can be suitably used. The article or material to be processed is placed in this packaging body, and the opening is sealed by heat sealing, etc. Thereafter, the whole packaging body can be sterilized in the sterilization apparatus.

The indicator of the present invention may be placed on the inner surface of the above-mentioned packaging body. There are no limitations on the methods for placing the indicator, and methods using adhesives, heat sealing, etc., can be used. In addition, the indicator can be provided by applying or printing the ink composition of the present invention directly to the inner surface of the packaging body. The indicator can be formed at the stage of manufacturing the packaging body by the application or printing of the ink composition.

It is preferable for the packaging body of the present invention to be provided with a transparent window portion in a part of the packaging body so that the indicator can be visually checked from the outside. For example, the indicator may be formed on the inner surface of the packaging body at a position in which the indicator can be visually recognized through a transparent sheet which is formed of a transparent sheet and a polyethylene synthetic paper.

Sterilization may be performed using the packaging body of the present invention by, for example, a method including the steps of: inserting an article or material to be processed into the packaging body; sealing the packaging body holding the article or material to be processed inside; and placing the packaging body in a hydrogen peroxide plasma sterilization atmosphere. More specifically, the material to be processed (e.g., medical instruments, foods, etc.) is placed in the packaging body, and then the packaging body is sealed with a known method, such as heat sealing or the like. Subsequently, the whole packaging body is placed in a hydrogen peroxide gas sterilization atmosphere. For example, the packaging body is placed in a sterilizing chamber of a known or commercially available sterilizer (e.g., a low-temperature plasma sterilization system), and sterilization is performed. After sterilization is completed, the whole packaging body is taken out and the material can be kept in the packaging body as it is until it is put to use. In this case, sterilization is preferably performed by placing the packaging body in a hydrogen peroxide gas sterilization atmosphere until the color of the color-changing layer of the Indicator changes.

EXAMPLES

The characteristics of the present invention will be described more clearly with reference to Examples and Comparative Examples. However, the scope of the present invention is not limited by the following Examples.

Examples 1 to 4 and Comparative Examples 1 to 2

The components shown in Table 1 were uniformly mixed with a stirrer, thereby preparing ink compositions. Specifically, a solvent, dye, and styrene acrylic resin or styrene-maleic acid resin were stirred with a dissolver. When the resin was difficult to dissolve, the resin was heated as required.

Subsequently, a non-color-changing coloring matter and a resin binder were introduced therein, followed by further stirring. Thereafter, the resultant mixture was cooled to room temperature, and a surfactant and an extender were added, followed by uniformly stirring, thereby obtaining an ink composition.

Comparative Examples 1 to 7

The same procedure as in Example I was followed except that the ink composition was changed as shown in Table 1, thereby preparing ink compositions.

The components shown in table 1 are specifically as follows.
1) C.I. Basic Violet 7: methine dye
2) C.I. Basic Orange 21: methine dye
3) C.I. Solvent Violet 8: triarylmethane dye
4) Microlith green G-T: non-coloring coloring matter, tradename "Microlith green G-T", product of Ciba Speciality Chemicals
5) Joncryl 690: styrene acrylic resin, tradename "Joncryl 690", product of Johnson Polymer
6) ARAKYD 700: a styrene-maleic acid resin, the product name "Arastar 700" product of Arakawa Chemical Industries
7) DENKA Butyral #2000L: polyvinyl butyral resin, tradename "DENKA Butyral #2000L" products of Denki Kagaku Kogyo K.K.
8) Versamid 756: polyamide resin, tradename "Versamid 756", product of Cognis Japan
9) NIKKOL CA-2150: quaternary-ammonium-salt surfactant, product name "NIKKOLCA-2150", product of Nikko Chemicals
10) Aerosil R-972: silica gel, tradename "Aerosil R-972" Japan aerosil
11) Butyl cellosolve: Solvent Test Example 1

Ink compositions of Examples and Comparative Examples were evaluated for color-changing properties.

Each ink composition was applied to a PET paper (50 mm×50 mm) using 250-mesh-screen printing to form a coating film, and the coating film was thoroughly dried. The resultant product was used as a test sample.

To evaluate the color-changing properties, the test sample was put in an airtight container with a temperature of 50° C. Subsequently, the pressure was reduced (pressure: 0.1 kPa), a hydrogen peroxide solution was poured into the container, and the test samples was exposed to the gasified hydrogen peroxide for 6 minutes. Three experiments were performed while setting the amount of hydrogen peroxide solution to be poured into the container as follows: Experiment 1: 2 mg/L of hydrogen peroxide solution, Experiment 2: 18 mg/L of hydrogen peroxide solution, and Experiment 3: 36 mg/L of hydrogen peroxide solution. After the exposure was complete, the color differences A between a blank sample (a sample before exposure) and the samples after exposure were measured. The measurement was performed using a commercially available color difference meter "OR-300 (product of Minolta)". The measurement results are shown in Table 1.

TABLE 1

| Composition | Examples | | | | Comparative Examples | |
|---|---|---|---|---|---|---|
| | 1 | 2 | 3 | 4 | 1 | 2 |
| C.I.Basic Violet 7 | 0.5 | 0.50 | 0.50 | | 0.50 | |
| C.I.Basic Orange 21 | | | | 0.50 | | |
| C.I.Solvent Violet 8 | | | | | | 0.50 |
| Microlith green G-T | 2.00 | | 2.00 | | 2.00 | |
| Joncryl 690 | 20.00 | | 20.00 | 20.00 | | |
| Arastar 700 | | 20.00 | | | | |
| DENKA Butyral #2000L | 10.00 | 10.00 | 10.00 | 10.00 | 20.00 | |
| Versamid 756 | | | | | | 20.00 |
| NIKKOL CA-2150 | 0.00 | 0.00 | 1.00 | 0.00 | 0.00 | 0.00 |
| Aerosil R-972 | 0.00 | 0.00 | 1.00 | 0.00 | 0.00 | 0.00 |
| Butyl Cellosolve | 60.50 | 69.50 | 58.50 | 69.50 | 74.50 | 79.50 |
| Total Effect | 93.00 | 100.00 | 93.00 | 100.00 | 97.00 | 100.00 |

TABLE 1-continued

|  | Examples | | | | Comparative Examples | |
| --- | --- | --- | --- | --- | --- | --- |
| Composition | 1 | 2 | 3 | 4 | 1 | 2 |
| Experiment 1 | 6.4 | 5.1 | 11.8 | 5.8 | 32.8 | 36.4 |
| Experiment 2 | 37.3 | 18.3 | 42.5 | 20.5 | 36.5 | 47.4 |
| Experiment 3 | 47.4 | 30.5 | 50.8 | 30.1 | 34.3 | 46.0 |

As is clear from the results shown in Table 1, in Experiments 1 to 3, the color changing at the early stage of exposure in Comparative Examples 1 and 2 was outstanding and the subsequent color-changing difference (difference in each color difference) was small, and therefore it was difficult to distinguish the difference with the naked eye. In contrast, the color changing differences can be recognized with the naked eye in Examples 1 to 4 because the differences in the color difference in each concentration were 5 or more.

The invention claimed is:

1. An ink composition for detecting hydrogen peroxide gas comprising 1) at least one of styrene acrylic resins and styrene-maleic acid resins, 2) a methine dye, and 3) a cationic surfactant,
    wherein 1) the content of said at least one of styrene acrylic resins and styrene-maleic acid resins is 1 to 50% by weight relative to the total weight of the composition,
    2) the content of the methine dye is 0.05 to 5% by weight relative to the total weight of the composition, and
    3) the cationic surfactant is at least one member selected from the group consisting of behenyltrimethylammonium chloride, hexadecyltrimethylammonium chloride, lauryltrimethylammonium chloride, and octadecyltrimethylammonium chloride, and
    wherein the content of the cationic surfactant is 0.1 to 15% by weight relative to the total weight of the composition.

2. The ink composition for detecting hydrogen peroxide gas according to claim 1, further comprising an extender.

3. The ink composition for detecting hydrogen peroxide gas according to claim 2, wherein a part or all of the extender is composed of silica.

4. The ink composition for detecting hydrogen peroxide gas according to claim 1, further comprising a second resin binder that excludes styrene acrylic resin and styrene-maleic acid resin.

5. The ink composition for detecting hydrogen peroxide gas according to claim 1, further comprising at least one of coloring matters whose colors do not change in a hydrogen peroxide gas atmosphere.

6. An indicator for hydrogen peroxide gas detection, comprising a color-changing layer including the ink composition according to claim 1.

7. The indicator according to claim 6, further comprising a non-color-changing layer whose color does not change in a hydrogen peroxide gas atmosphere.

8. The indicator according to claim 6, wherein
    (1) difference between a color difference value $\Delta_{2mg}$ before and after the exposure to 2mg/L of hydrogen peroxide gas for 6 minutes at a temperature of 50° C. and a color difference value $\Delta_{18mg}$ before and after the exposure to 18mg/L of hydrogen peroxide gas for 6 minutes at a temperature of 50° C. is 5 or more, and
    (2) difference between a color difference value $\Delta_{18mg}$ before and after the exposure to 18mg/L of hydrogen peroxide gas for 6 minutes at a temperature of 50° C. and a color difference value $\Delta_{36mg}$ before and after the exposure to 36mg/L of hydrogen peroxide gas for 6 minutes at a temperature of 50° C. is 5 or more.

9. A packaging body for use in hydrogen peroxide gas sterilization, comprising an indicator for hydrogen peroxide gas detection, formed on an inner surface of a gas permeable packaging body,
    wherein the indicator for hydrogen peroxide gas detection comprising a color-changing layer comprising an ink composition for detecting hydrogen peroxide gas comprising 1) at least one of styrene acrylic resins and styrene-maleic acid resins, 2) a methine dye, and 3) a cationic surfactant,
    wherein 1) the content of said at least one of styrene acrylic resins and styrene-maleic acid resins is 1 to 50% by weight relative to the total weight of the composition,
    2) the content of the methine dye is 0.05 to 5% by weight relative to the total weight of the composition, and
    3) the cationic surfactant is at least one member selected from the group consisting of behenyltrimethylammonium chloride, hexadecyltrimethylammonium chloride, lauryltrimethylammonium chloride, and octadecyltrimethylammonium chloride, and
    wherein the content of the cationic surfactant is 0.1 to 15% by weight relative to the total weight of the composition.

10. The packaging body according to claim 9, wherein a transparent aperture is provided in part of the packaging body in such a manner that the indicator can be checked from the outside.

11. The packaging body according to claim 9, wherein the gas permeable packaging body is formed of polyethylene fiber.

12. The hydrogen peroxide gas sterilization method comprising the steps of:
    (i) charging a material to be treated into a gas permeable packaging body for use in hydrogen peroxide gas sterilization,
    wherein the gas permeable packing body comprises an indicator for hydrogen peroxide gas detection, formed on an inner surface of said gas permeable packaging body,
    wherein the indicator comprises a color-changing layer that includes an ink composition for detecting hydrogen peroxide gas,
    wherein the ink composition for detecting hydrogen peroxide gas comprises 1) at least one of styrene acrylic resins and styrene-maleic acid resins, 2) a methine dye, and 3) a cationic surfactant,
    wherein 1) at least one of styrene acrylic resins and styrene-maleic acid resins includes 1 to 50% by weight of the composition, and 2) a methine dye includes 0.05 to 5% by weight of the composition,
    wherein 3) the cationic surfactant is at least one member selected from the group consisting of behenyltrimethylammonium chloride, hexadecyltrimethylammonium chloride, lauryltrimethylammonium chloride, and octadecyltrimethylammonium chloride, and
    wherein the content of the cationic surfactant is 0.1 to 15% by weight relative to the total weight of the composition, (ii) sealing the gas permeable packaging body charged with the material to be treated; and (iii) placing the gas permeable packaging body in a hydrogen peroxide plasma sterilization atmosphere.

13. The method according to claim 12, wherein the packaging body is kept in the hydrogen peroxide gas sterilization atmosphere until the color of the color-changing layer of the indicator changes.

14. An ink composition for detecting hydrogen peroxide gas comprising 1) styrene acrylic resins, 2) a methine dye, and 3) a cationic surfactant, wherein 1) the content of said styrene acrylic resins is 1 to 50% by weight relative to the total weight of the composition, 2) the content of the methine dye is 0.05 to 5% by weight relative to the total weight of the composition, and 3) the cationic surfactant is at least one member selected from the group consisting of behenyltrimethylammonium chloride, hexadecyltrimethylammonium chloride, lauryltrimethylammonium chloride, and octadecyltrimethylammonium chloride, and wherein the content of the cationic surfactant is 0.1 to 15% by weight relative to the total weight of the composition.

15. An indicator for hydrogen peroxide gas detection, comprising a color-changing layer including the ink composition according to claim 14.

16. An ink composition for detecting hydrogen peroxide gas comprising 1) styrene-maleic acid resins, 2) a methine dye, and 3) a cationic surfactant, wherein 1) the content of said styrene-maleic acid resins is 1 to 50% by weight relative to the total weight of the composition, 2) the content of the methine dye is 0.05 to 5% by weight relative to the total weight of the composition, and 3) the cationic surfactant is at least one member selected from the group consisting of behenyltrimethylammonium chloride, hexadecyltrimethylammonium chloride, lauryltrimethylammonium chloride, and octadecyltrimethylammonium chloride, and wherein the content of the cationic surfactant is 0.1 to 15% by weight relative to the total weight of the composition.

17. An indicator for hydrogen peroxide gas detection, comprising a color-changing layer including the ink composition according to claim 16.

\* \* \* \* \*